(12) United States Patent
Alfano et al.

(10) Patent No.: US 8,974,444 B2
(45) Date of Patent: Mar. 10, 2015

(54) METHOD FOR PICOSECOND AND FEMTOSECOND LASER TISSUE WELDING

(75) Inventors: Robert R. Alfano, Bronx, NY (US); Vidyasagar Sriramoju, Dobbs Ferry, NY (US)

(73) Assignee: Robert R. Alfano, Bronx, NY (US)

( * ) Notice: Subject to any disclaimer, the term of this patent is extended or adjusted under 35 U.S.C. 154(b) by 0 days.

(21) Appl. No.: 13/642,746

(22) PCT Filed: Apr. 20, 2011

(86) PCT No.: PCT/US2011/033231
§ 371 (c)(1),
(2), (4) Date: Jun. 3, 2013

(87) PCT Pub. No.: WO2011/133660
PCT Pub. Date: Oct. 27, 2011

(65) Prior Publication Data
US 2013/0245616 A1  Sep. 19, 2013

Related U.S. Application Data

(60) Provisional application No. 61/326,026, filed on Apr. 20, 2010.

(51) Int. Cl.
*A61B 18/20* (2006.01)
*A61B 17/00* (2006.01)
*A61B 18/00* (2006.01)

(52) U.S. Cl.
CPC ............. *A61B 18/20* (2013.01); *A61B 18/203* (2013.01); *A61B 2017/00508* (2013.01); *A61B 2018/00452* (2013.01)
USPC ............. 606/3; 607/89; 600/476; 359/326; 128/898

(58) Field of Classification Search
CPC .......... A61M 5/178; A61F 17/20; A61F 1/03; A61F 13/20; A61B 17/10; A61B 17/04; A61B 17/88; A61B 17/32; A61B 17/00; A61B 18/18; A61B 6/00; A61B 19/00; A61N 5/06; G02F 1/35
USPC ................. 606/4, 8, 12, 6, 3, 9, 15; 600/476; 607/89; 359/326; 128/898
See application file for complete search history.

(56) References Cited

U.S. PATENT DOCUMENTS 4,929,246 A * 5/1990 Sinofsky ............................ 606/8
5,071,417 A * 12/1991 Sinofsky ............................ 606/8
(Continued)

FOREIGN PATENT DOCUMENTS

EP    1958584 A1 * 8/2008

OTHER PUBLICATIONS

Martin Chaplin Water Structure and Science http://creativecommons.org/licenses/by-nc-nd/2.0/uk/, pp. 1-6 mailto:martin.chaplin@btinternet.com?subject=from_water_web_site.*
(Continued)

*Primary Examiner* — William Thomson
*Assistant Examiner* — Victor Shapiro
(74) *Attorney, Agent, or Firm* — Myron Greenspan; Lackenbach Siegel LLP

(57) ABSTRACT

A method for welding tissue wounds in an animal. The method comprises joining edges of a tissue wound and irradiating the tissue wound and tissue surrounding the tissue wound with a pulsed laser. The pulsed laser has a laser wavelength in a range of an absorption band of water, elastin and/or collagen in the tissue wound and tissue surrounding the tissue wound. The pulsed laser has a pulse width of not more than picoseconds in order of magnitude to heat tissue surrounding the tissue wound and facilitate bonding of native tissue protein present in the tissue surrounding the tissue wound to achieve tissue repair. The laser wavelength is in a range of between about 800 nm to about 2,700 nm.

24 Claims, 14 Drawing Sheets

(56) References Cited

U.S. PATENT DOCUMENTS

| | | | |
|---|---|---|---|
| 5,269,778 A * | 12/1993 | Rink et al. | 606/12 |
| 5,571,216 A * | 11/1996 | Anderson | 128/898 |
| 6,146,375 A * | 11/2000 | Juhasz et al. | 606/6 |
| 6,346,101 B1 * | 2/2002 | Alfano et al. | 606/15 |
| 6,583,117 B2 * | 6/2003 | Owen et al. | 424/443 |
| 2003/0028228 A1 * | 2/2003 | Sand | 607/89 |
| 2004/0092913 A1 * | 5/2004 | Hennings et al. | 606/3 |
| 2004/0176752 A1 * | 9/2004 | Alfano et al. | 606/4 |
| 2005/0240107 A1 * | 10/2005 | Alfano et al. | 600/476 |
| 2006/0161142 A1 * | 7/2006 | Sierra et al. | 606/9 |
| 2007/0219601 A1 * | 9/2007 | Neuberger | 607/89 |
| 2008/0225383 A1 * | 9/2008 | Theberge et al. | 359/326 |
| 2009/0306707 A1 * | 12/2009 | Brownlee et al. | 606/214 |

OTHER PUBLICATIONS

United States Patent and Trademark Office Apr. 29, 2011 Certified Foreign Priority Application.*

* cited by examiner

Non Thermal Mechanisms (Indirect)

Direct Collagen/Elastin Excitation Mechanisms

METHOD FOR PICOSECOND AND FEMTOSECOND LASER TISSUE WELDING

CROSS-REFERENCE TO RELATED APPLICATION

This application claims the benefit of and priority to U.S. Provisional application Ser. No. 61/326,026 filed Apr. 20, 2010, the contents of which are incorporated by reference.

GOVERNMENT RIGHTS

This invention was made with Government support from the NIH #5R01EB000297-06.

FIELD OF THE INVENTION

This invention relates to laser tissue welding and a method for using pulsed lasers to weld or seal a wound in a tissue.

BACKGROUND

Laser tissue welding (LTW) is a promising alternative to wound repair using conventional techniques such as sutures, staples and clips.

Small amounts of injury to delicate structures, such as those inflicted in microsurgery, can cause wound closure to fail. Practitioners with the surgical skills at a level necessary to perform these types of repairs are limited.

Suturing is slow and difficult to perform through an endoscope. The limits to stapler miniaturization reduce the scope of endoscopic surgery, whereas its introduction can convert many open surgeries to an endoscopic approach. Further, suture repairs are usually not completely watertight. Leakage can occur in the gaps between sutures and needle holes.

LTW has recently received much attention because of its potential advantages, applicable in all branches of surgery: rapid wound healing, reduced surgical time, less foreign body reactions, little or no fibrosis, no chance of stricture or stenosis development, immediate intraoperative watertight sealing and non-lithogenicity over conventional wound closure methods. Wounds treated by LTW have minimal inflammatory response, near-normal collagen content, minimal residue breaks and disorientation in the collagen and elastin fibers.

LTW can be used in, but not limited to, microsurgery, watertight sealing, endoscopic surgery and cosmetic surgery.

LTW reduces these technician demands and deficiencies in the conventional techniques.

SUMMARY OF THE INVENTION

Accordingly, disclosed is a method for welding tissue wounds in an animal. The method comprises joining edges of a tissue wound and irradiating the tissue wound and tissue surrounding the tissue wound with a pulsed laser. The pulsed laser has a laser wavelength in a range of an absorption band of water, elastin and/or collagen in the tissue wound and tissue surrounding the tissue wound. The pulsed laser has a pulse width of not more than picoseconds in order of magnitude to non-thermally vibrate molecules in tissue surrounding the tissue wound and facilitate bonding of native tissue protein present in the tissue surrounding the tissue wound to achieve tissue repair.

The laser wavelength is in a range of between about 800 nm to about 2,700 nm.

The pulsed laser can be a picosecond laser and/or a femtosecond laser. The pulse width is less than 10 picoseconds in length.

The tissue wound can be skin, mucosal tissue, bone, blood vessels, neural tissue, hepatic tissue, pancreatic tissue, splenic tissue, renal tissue, bronchial tissue, tissues of the respiratory tract, tissues of the urinary tract, tissues of the gastrointestinal tract and tissues of the gynecologic tract. For example, the tissue wound can be a fistula of the gastrointestinal tract, a fistula of the urinary tract and/or an air leak in pulmonary tissue.

The animal can be a human.

Also disclosed is a method for welding tissue wounds in animals. The method comprises joining edges of a tissue wound and irradiating the tissue wound and tissue surrounding the tissue wound with a picosecond or a femtosecond pulsed laser. The picosecond or femtosecond pulsed laser induces molecular crosslinking of tissue proteins surrounding the tissue wound and facilitates bonding of native tissue proteins present in the tissue surrounding the tissue wound to achieve tissue fusion.

The picosecond or the femtosecond pulsed laser can be picosecond or femtosecond solid state lasers, semiconductor lasers and fiber lasers, YAG glass lasers, and parametric oscillator lasers.

The picosecond or the femtosecond pulsed laser is tuned to a spectral range which corresponds to an absorption band of water in the tissue wounds and tissue proteins surrounding the wounds at wavelengths about 1064+/−30 nm, 1450+/−30 nm, 1560+/−30 nm, 1950+/−30 nm and 2400+/−30 nm. When irradiating, the water in the tissue wound and tissue proteins surrounding the tissue wound absorbs energy from the picosecond or femtosecond pulsed laser by vibrational overtones and combinations of primary modes (v1, v2, v3) and non-thermally excites water mediated hydrogen bonds in collagen and elastin molecules due to energy transfer. If the picosecond or the femtosecond pulsed laser has wavelengths of 1560+/−30 nm, energy at these wavelengths excites a combination mode (1, 0, 1) of water. If the wavelengths of 1064+/−30 nm are used, the laser excites a combination mode (1, 1, 1) and disrupts the hydrogen-bonding in the collagen and elastin molecules.

Alternatively, the picosecond or the femtosecond pulsed laser is tuned to a spectral range which corresponds to an absorption band of collagen in the tissue wounds and tissue proteins surrounding the tissue wounds at wavelengths of 1750+/−30 nm, 2050+/−30 nm, 2200+/−30 nm, and 2300+/−30 nm. When irradiating, the tissue proteins absorb energy from the picosecond or femtosecond pulsed laser by vibrational overtones and combinations modes (v1, v2, v3) and non-thermally excites collagen molecules by direct energy transfer. Energy of the picosecond or the femtosecond pulsed laser at these wavelengths excites combination modes, and overtone vibrational modes of the collagen, and disrupt hydrogen-bonding in structural protein collagen molecules.

Alternatively, the picosecond or the femtosecond pulsed laser is tuned a spectral range which corresponds to an absorption band of elastin in the tissue wound and tissue proteins surrounding the tissue wound at wavelengths 1700+/−30 nm, 2050+/−30 nm, 2200+/−30 nm, and 2300+/−30 nm. When irradiating, the tissue proteins absorb energy from the picosecond or femtosecond pulsed laser by vibrational overtones and combinations modes (v1, v2, v3) and non-thermally excites elastin molecules by direct energy transfer. Energy of the picosecond or the femtosecond pulsed laser at these wavelengths excites combination modes, and overtone vibrational modes of the elastin, and disrupt hydrogen-bonding in structural protein elastin molecules.

The average power of the picosecond or femtosecond pulsed laser is in a range of about 40 miliwatts to about 400 miliwatts to induce non-thermal mechanisms of reversible dissociation of intramolecular, intermolecular hydrogen bonds, and electrostatic interactions in tissue proteins surrounding the tissue wound. Alternatively, the average power of the picosecond and the femtosecond pulsed laser(s) is in a range of 100 miliwatts to 1600 miliwatts to induce the thermal mechanisms of reversible dissociation of intramolecular, intermolecular hydrogen bonds, and electrostatic interactions in tissue proteins surrounding the tissue wound.

The animals can be a human and/or other mammals.

The tissue wound can be skin, mucosal tissue, bone, blood vessels, neural tissue, hepatic tissue, pancreatic tissue, splenic tissue, renal tissue, bronchial tissue, tissues of the respiratory tract, tissues of the urinary tract, tissues of the gastrointestinal tract and tissues of the gynecologic tract, tissues of male reproductive system.

The picosecond or the femtosecond pulsed laser has a pulse width of less than 10 ps for tissue welding using a wavelength in a range of about 800 nm to about 2700 nm. Both picosecond and femtosecond pulses can be emitted from the picosecond or femtosecond pulsed laser.

Additionally, a plurality of picosecond or femtosecond pulsed lasers can be used to irradiate the tissue wound and tissue surrounding the tissue wound.

BRIEF DESCRIPTION OF THE DRAWINGS

These and other features, benefits, and advantages of the present invention will become apparent by reference to the following figures, with like reference numbers referring to like structures across the views, wherein:

FIGS. 7A-12B illustrate results of a comparative analysis of repair of a wound site in accordance with the invention, repair of a wound site using CW LTW and repair of a wound site with suture, where FIGS. 7A and 7B illustrate results from Femtosecond pulsed lasers repair after seven postoperative days.

DETAILED DESCRIPTION OF THE INVENTION

Collagen is the main structural protein of the body. Elastin is a protein in connective tissue that is elastic and allows many tissues in the body to resume their shape after stretching and contracting. Elastin helps skin to return to its original position when it is poked or pinched. Elastin serves as important function in arteries as a medium for pressure wave propagation to help blood flow. Elastin is also very important in the lungs, elastic ligaments, the skin, and the bladder, elastic cartilage.

An LTW procedure involves illuminating re-approximated edges of bisected tissue with a laser beam at an appropriate wavelength which is absorbed by the tissue.

Figure 1:
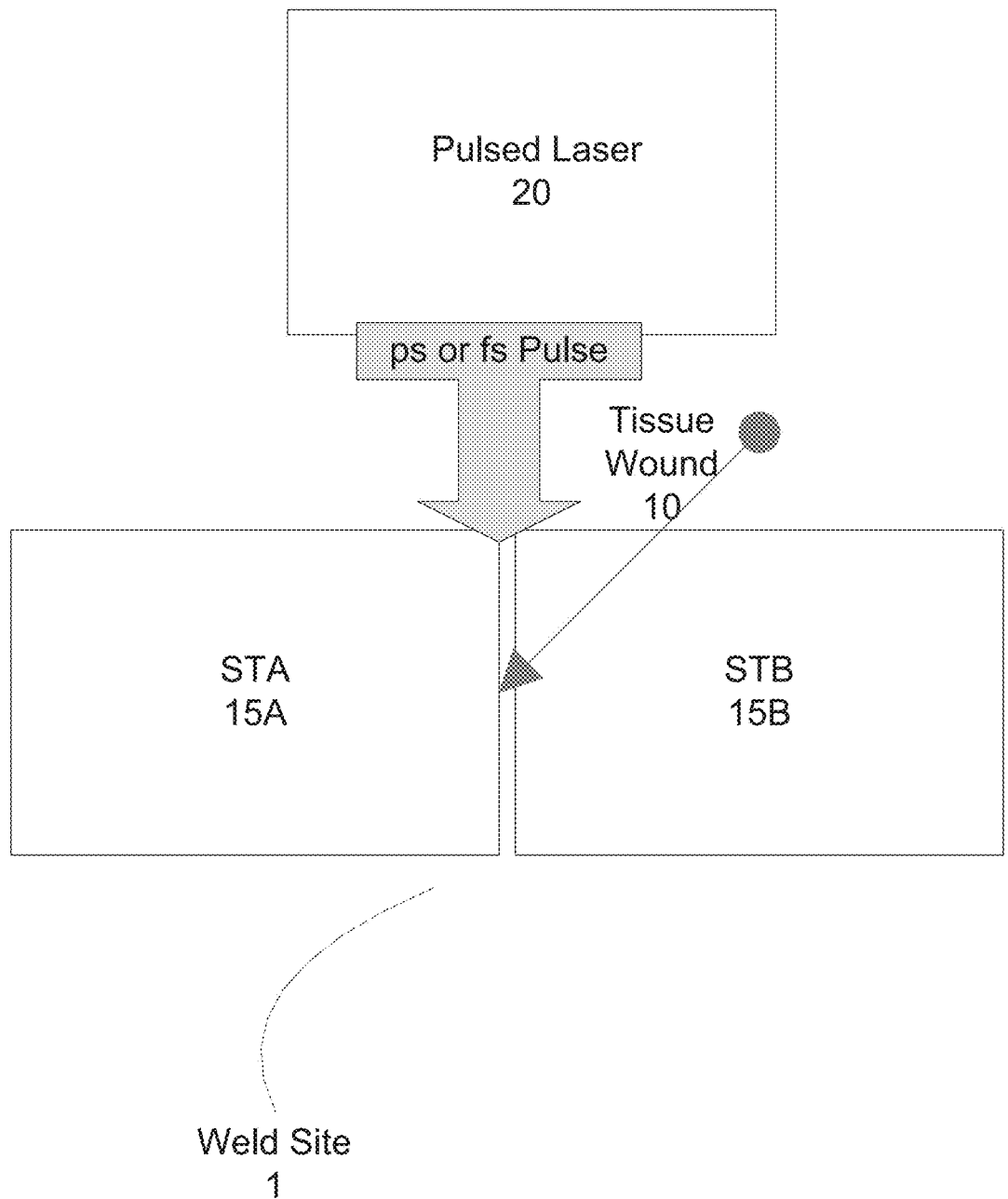
FIG. 1 illustrates an exemplary weld site.

FIG. 1 illustrates an exemplary weld site 1. The weld site 1 is located by a tissue wound 10. The tissue wound 10 is surrounded by protein tissue STA and STB (referenced as "15A" and "15B" and collectively 15) on each side of the tissue wound 10. The method for LTW described herein uses an ultra-short pulsed laser ("pulsed laser" depicted as "20" in FIG. 1). The pulsed laser 20 has a pulse width less than picoseconds ("ps") or femtoseconds ("fs") in order of magnitude. Pulse width as used herein refers to the on-time of a pulse of the laser. LTW is applicable to human clinical and surgical procedures using the fs or ps pulsed lasers 20. The ps or fs Pulse (not labeled) is depicted in FIG. 1 being emitted from the pulsed laser 20 and irradiating the weld site 1.

The pulsed laser 20 excites combinations and overtones vibrations of water, collagen, and elastin of surrounding tissue 15 to couple together to form bonds and fuse the surrounding tissue together.

The scattering length and absorption coefficient of the surrounding tissue 15 determines the penetration depth of the light, and hence, the thickness of the weld that can be attained. Laser welding can be readily performed endoscopically. This may extend the range of procedures that can be converted from the open to endoscopic approach.

The salient properties of laser light, such as, but not limited to, wavelength, polarization, power, focal spot size, and pulse width, can be adjusted to optimize the efficacy of tissue welding. The properties can be adjusted prior to or during the welding. Additionally, optimum welding is achieved when the laser penetration depth matches the thickness of the tissue to be welded.

The method uses ps or fs pulses having a wavelength of near infrared radiation ("NIR") in a range of 800 to 2700 nm. NIR pulsed lasers can directly excite and activate the collagen/elastin molecules by matching the wavelengths of the pulsed laser to that of collagen/elastin NIR absorption overtones at about 1400 nm-2400 nm wavelengths (1750 nm, 2050 nm, 2200 nm, 2300 nm and 2350 nm for collagen, each +/−30 nm or each +/−20 nm), and (1700 nm, 2050 nm, 2200 nm and 2300 nm for elastin, each +/−30 nm or +/−20 nm, excluding the water absorption band at 1930 nm). Additionally, the ps or fs pulses can be used to excite water molecules and indirectly excite the collagen/elastin molecule using a wavelength about 1064 to 1600 μm, +/−30 nm or +/−20 nm and 1930+/−30 or +/−20 and 2400+/−30 nm or +/−20 nm.

The average powers for the pulsed laser is in a range of about 40 miliwatts to about 400 miliwatts depending on type of tissue, desired weld time and other factors. Below 40 miliwatts, there is not enough power to induce non-thermal mechanisms of reversible dissociation of intramolecular, intermolecular hydrogen bonds, electrostatic interactions in tissue proteins. Alternatively, the average power for the pulsed laser can be in a range of about 100 miliwatts to about 1600 miliwatts to induce the thermal mechanisms of reversible dissociation of intramolecular, intermolecular hydrogen bonds, electrostatic, and interactions in the structural proteins of the biological tissues.

The method uses the intrinsic chromophore molecular crosslinking of collagen and elastin of biological tissues by using the lasers tuned to vibrational overtones and combination modes of water as well as collagen/elastin molecules in tissue to match the overtones and combination modes of water and collagen/elastin at NIR wavelengths from 800 to 2700 nm.

Figure 2:
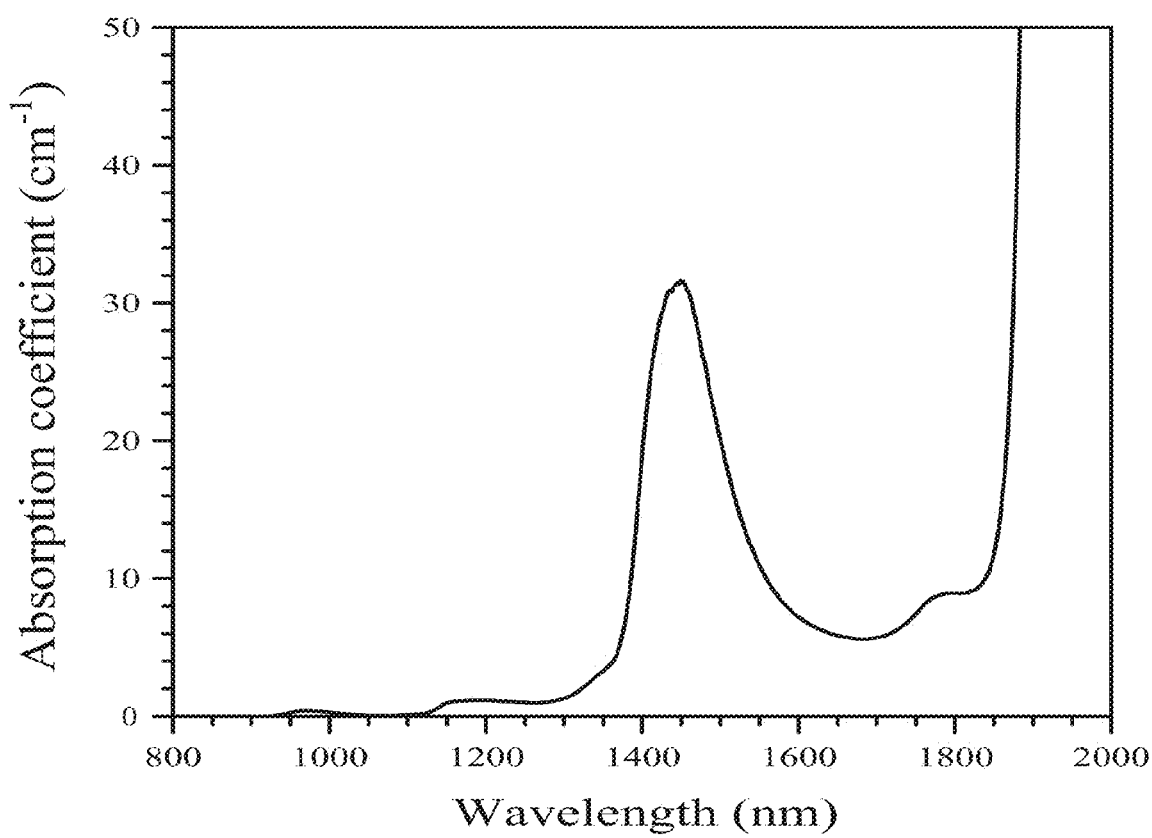
FIG. 2 illustrates a chart of the relationship between the wavelength and absorption coefficient for water.

As noted above, penetration depth can be controlled by changing the laser wavelength so that the water absorption coefficient matches the desired penetration depth. FIG. 2 illustrates a chart of the relationship between the wavelength and absorption coefficient. Use of ps or fs pulses can invoke non-thermal mechanisms, such as electronic or vibrational processes while reducing collateral damage to surrounding tissue, and still producing strong bonding.

The method described herein can be used for many different tissue types and areas of surgery. For example, the method can be used for coronary arterial surgery, repair of trauma to veins and arteries, asteriovenous shunt; and intra-cranial vascular surgery. The major protein is elastin. Additionally, the methods can be used for plastic surgery, surgical incision, lacerations from trauma with reduced scarring. The major protein is collagen. Additionally, the method can be used to seal pulmonary air leaks and fistulas in the gastrointestinal tract, such as, but not limited to, intestinal and urinary fistulas. Furthermore, the methods described herein may also be used to seal or weld animal or human tissue including, but not limited to, skin, mucosal tissue, bone, blood vessels, neural tissue, hepatic tissue, pancreatic tissue, splenic tissue, renal tissue, bronchial tissue, tissues of the respiratory tract, tissues of the urinary tract, tissues of the gastrointestinal tract and tissues of the gynecologic tract.

During indirect welding mechanisms, water in the tissue absorbs the laser energy and subsequently heats the collagen helix. When the collagen tissue temperature rises above 60° C., bonding is disrupted and partial dissociation occurs, followed by covalent and/or noncovalent bonding of the tissue protein molecules as the tissue cools. Successful welding requires precise control of laser power and exposure times to control tissue temperature and dehydration.

The collagen molecules, after secretion by the cells, assemble into characteristics fibers responsible for functional integrity of tissues, such as, skin, cornea, bone, cartilage, and tendon. They contribute a structural framework to other tissues, such as, blood vessels and most organs. Crosslinks between adjacent molecules are a prerequisite for the collagen fibers to withstand the physical stresses to which they are exposed. Collagen forms a triple helical structure. Every third amino acid is glycine (Gly), and a high proportion of the remaining residues are proline (Pro) and hydroxyproline (Hyp). The most common triplet combination in collagen is Gly-Pro-Hyp. The Hyp residue's hydroxyl group was shown to increase the thermal stability of the triple helix.

Figure 3:
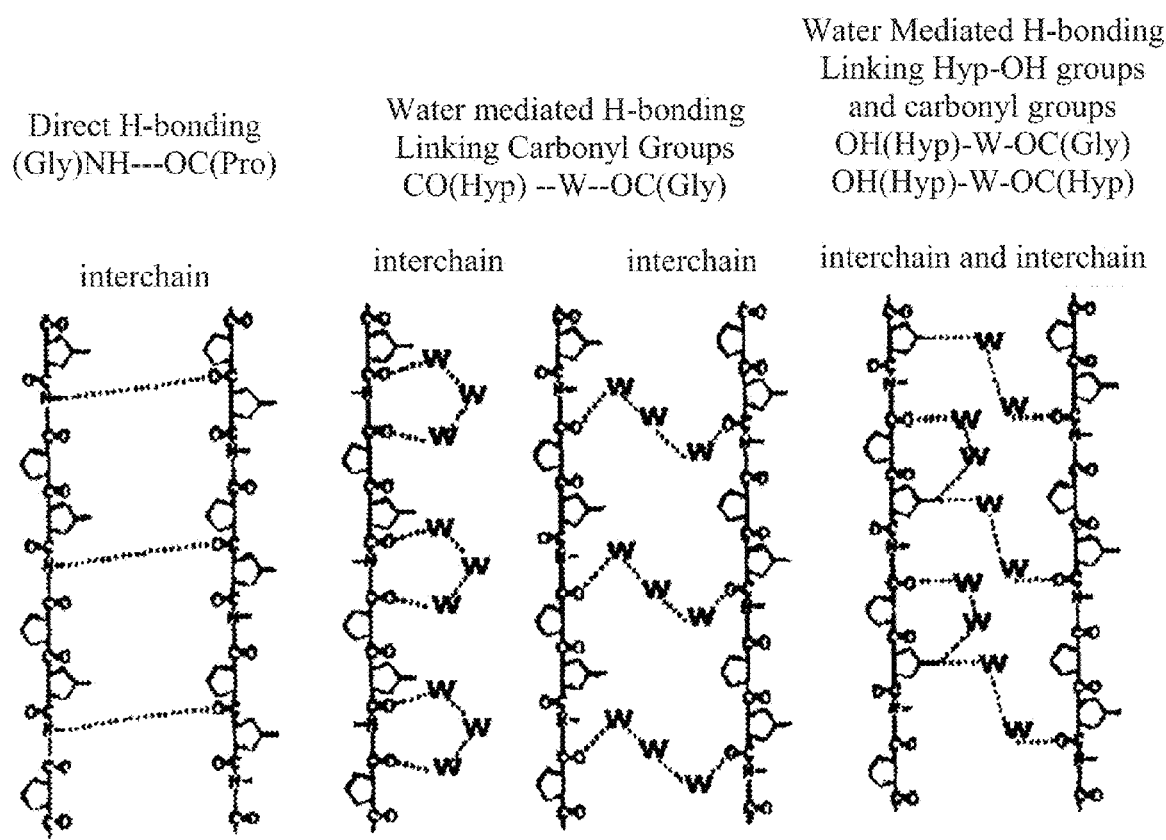
FIGS. 3A-3C illustrate different water bonds in a collagen chain.

FIGS. 3A-3C illustrates different water bonds in a collagen chain. Hydration plays an important role in maintaining the collagen helical structure. Interstitial water is separated into two distinct classes: tightly bound, and free water. The bound water stabilizes the collagen helix. Water mediated H-bonding is found in intra- and inter-chain bonds linking two carbonyl groups (CO(Hyp)-H$_z$O—CO(Gly); or OH groups to carbonyl groups (OH—Hz0-CO(Gly) or OH—H20-CO (Hyp)). The bound water maintains the distance between the chains and prevents collapse of the collagen helix. FIG. 3A shows direct H-bonding in the helix while the middle and right sides show water (indicated by w in FIG. 3A) mediated intrachain (between amino acids on the same chain) and interchain (between amino acids on different chains) hydrogen bonding. The water maintains the structure and spacing of helices as well as the chains.

Photo excitation of the 0-H stretch vibrations of the water molecules using the ps or fs pulsed laser weakens the intrachain and interchain bonds until the water molecules relax. While vibrational modes are excited, the water molecules may become mobile and move along the helix. The relaxation lifetime of the optical excited vibrations is on the order of 3 ps.

According to a Raman spectrum of collagen in the aorta the key modes and associated frequencies are: Amide I, 1660 cm$^-$; C=C bending of phenylalanine at 1591 cm$^{-1}$, CH2 bending mode of proteins at 1458 cm$^{-1}$, CH3CH2 twisting mode at 1321 cm$^{-1}$, amide III at 1277 cm$^{-1}$, CN stretching mode at 1123 cm$^{-1}$, ring breathing mode of phenylalanine at 1014 cm$^{-1}$, C—C stretching mode of proline at 935 cm$^{-1}$, C—C stretch of hydroxyproline at 868 cm$^{-1}$, and C—H inplane bending mode at 722 cm$^{-1}$.

The three primary vibrational energies of water responsible for overtone and combination absorption are: the OH symmetric stretching mode, v1 at 3500 cm$^{-1}$; the OH bending mode, v2 at 1598 cm$^{-1}$; and the asymmetric OH stretching mode, v3 at 3290 cm$^{-1}$. Changes in separation between collagen helices are reflected in the Raman spectra of O-H and N-H vibrational bands in the 3100 to 3800 cm-' range. Excitations in H$_2$0 molecules may excite collagen and hydrogen bonding bands. The v2 bending mode of water is near resonant with the amide I band of collagen allowing for efficient energy transfer between these two modes. The combination vibrational modes (1, 1, 1) are responsible for H$_2$O absorption at 1064 nm and combination mode (1, 0, 1) is responsible for H$_2$O absorption at 1560 nm.

Figure 4:
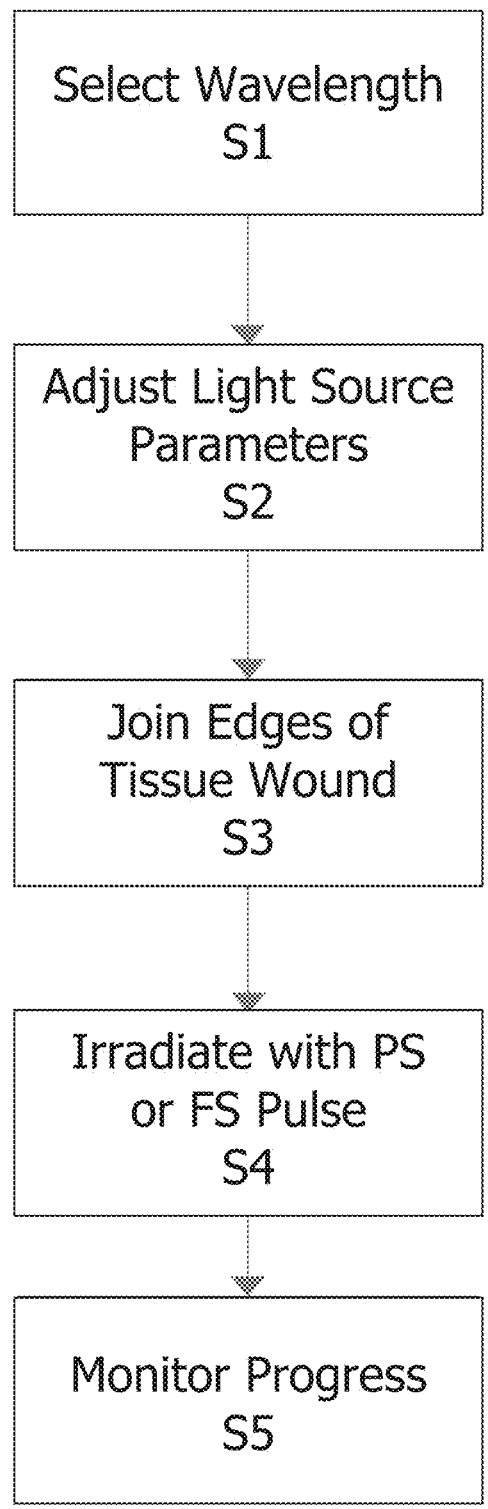
FIG. 4 illustrates an exemplary method for LTW in accordance with the invention.

FIG. 4 illustrates an exemplary method for LTW in accordance with the invention. At S1, a laser wavelength is selected. This selection is based upon a type of weld site 1, e.g., the type of tissue proteins subject to welding and the desired penetration depth. The pulsed laser 20 can be tailored to the tissue under repair. As described herein, the pulsed laser 20 in the NIR spectral region from 800 to 2700 nm that coincides with a resonance in the absorption spectrum of water and for elastin and collagen is used. The variation in the penetration depth is a function of the change in water absorption maximum to minimum over the range of the light source.

Strong absorption in the 1400 nm region has a tissue penetration depth of about 0.1 mm while light at 1300 nm may penetrate more deeply to 5 mm into the tissue. This large degree of penetration depths makes it feasible to optimize the welding process for a wide variety of tissue types using the pulsed laser 20. Additionally, laser light has a high degree of brightness and directionality as compared to other light sources. This means that tighter focal spots may be created with higher positioning accuracy using laser light than light from other sources.

Figure 5A:
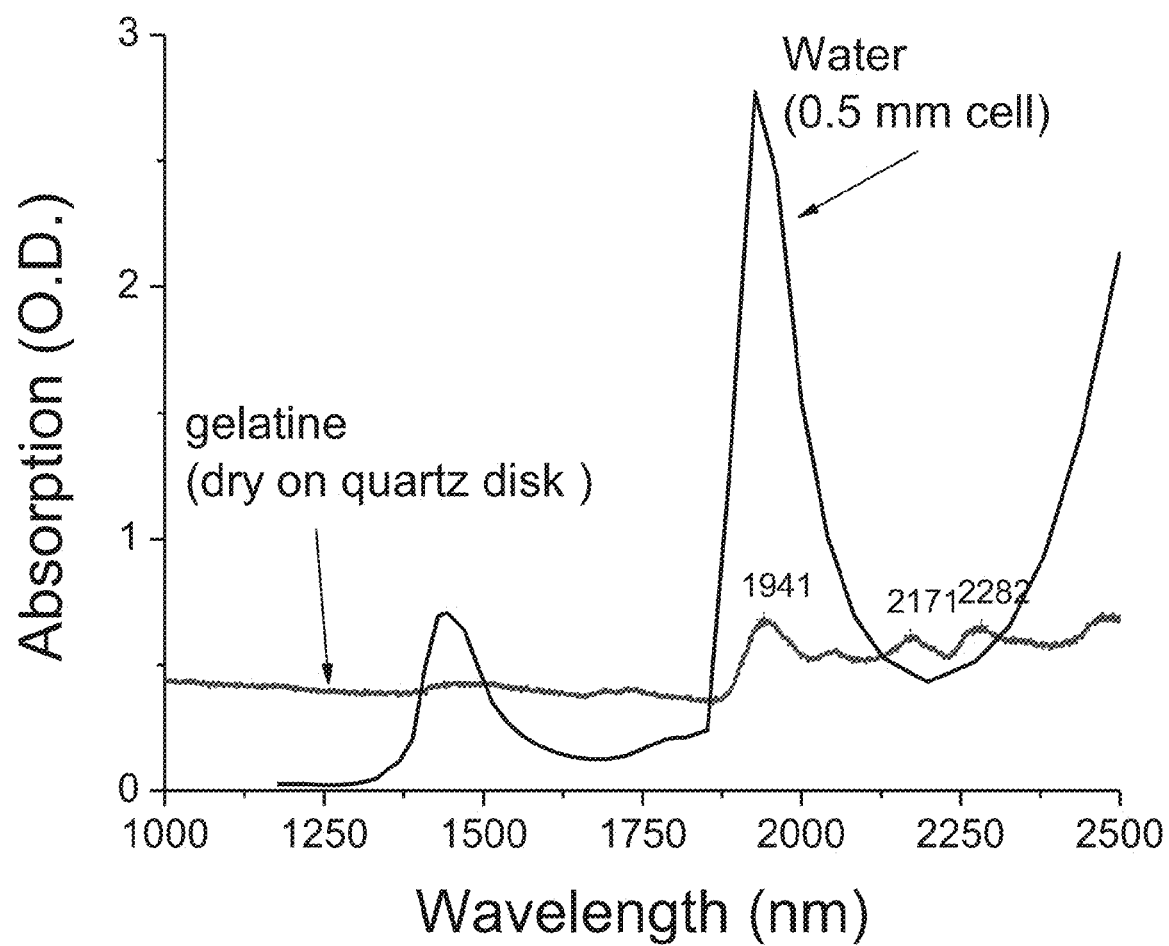
FIGS. 5A-5C illustrate charts for absorption spectrum for gelatin (fragmental collagen) and water (FIG. 5A), Collagen III (FIG. 5B), and Elastin (FIG. 5C)
Figure 5B:
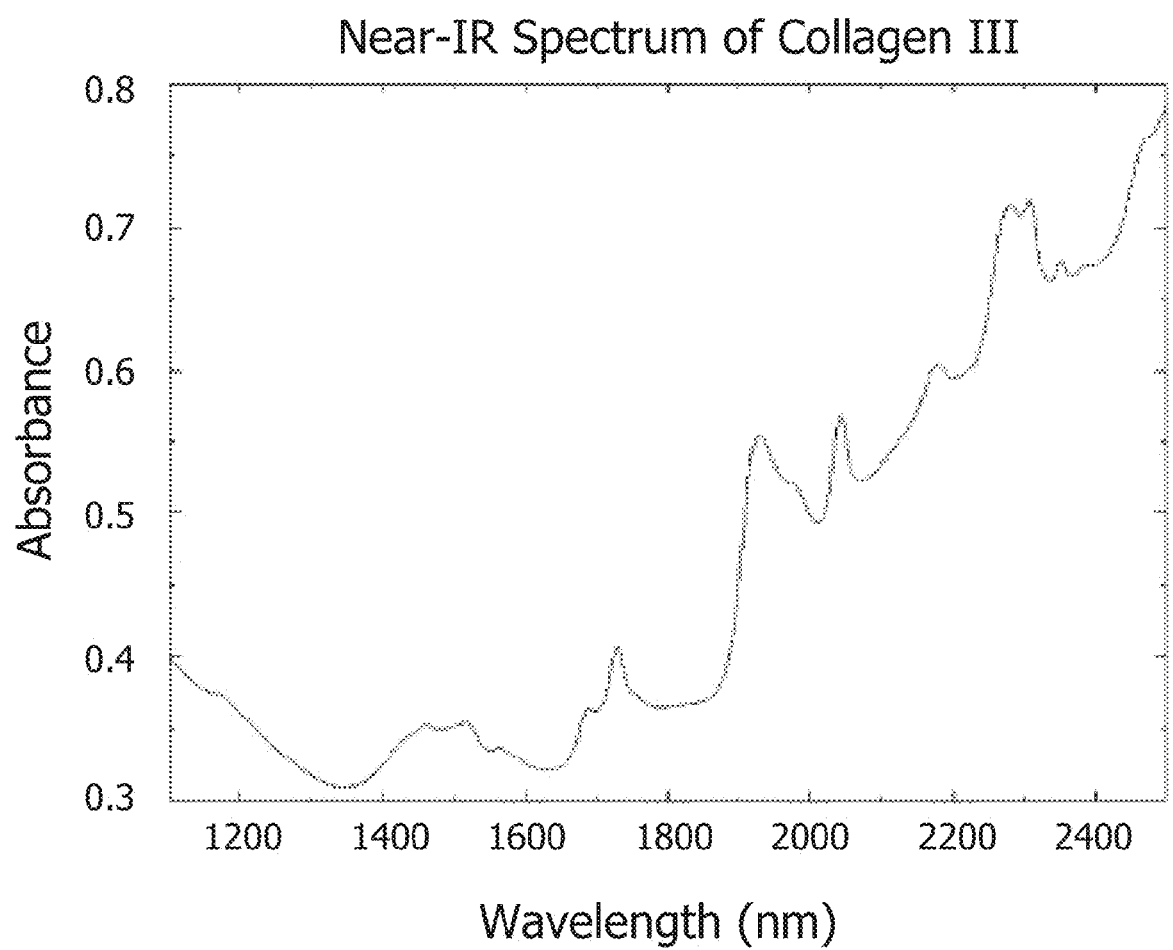
Figure 5C:
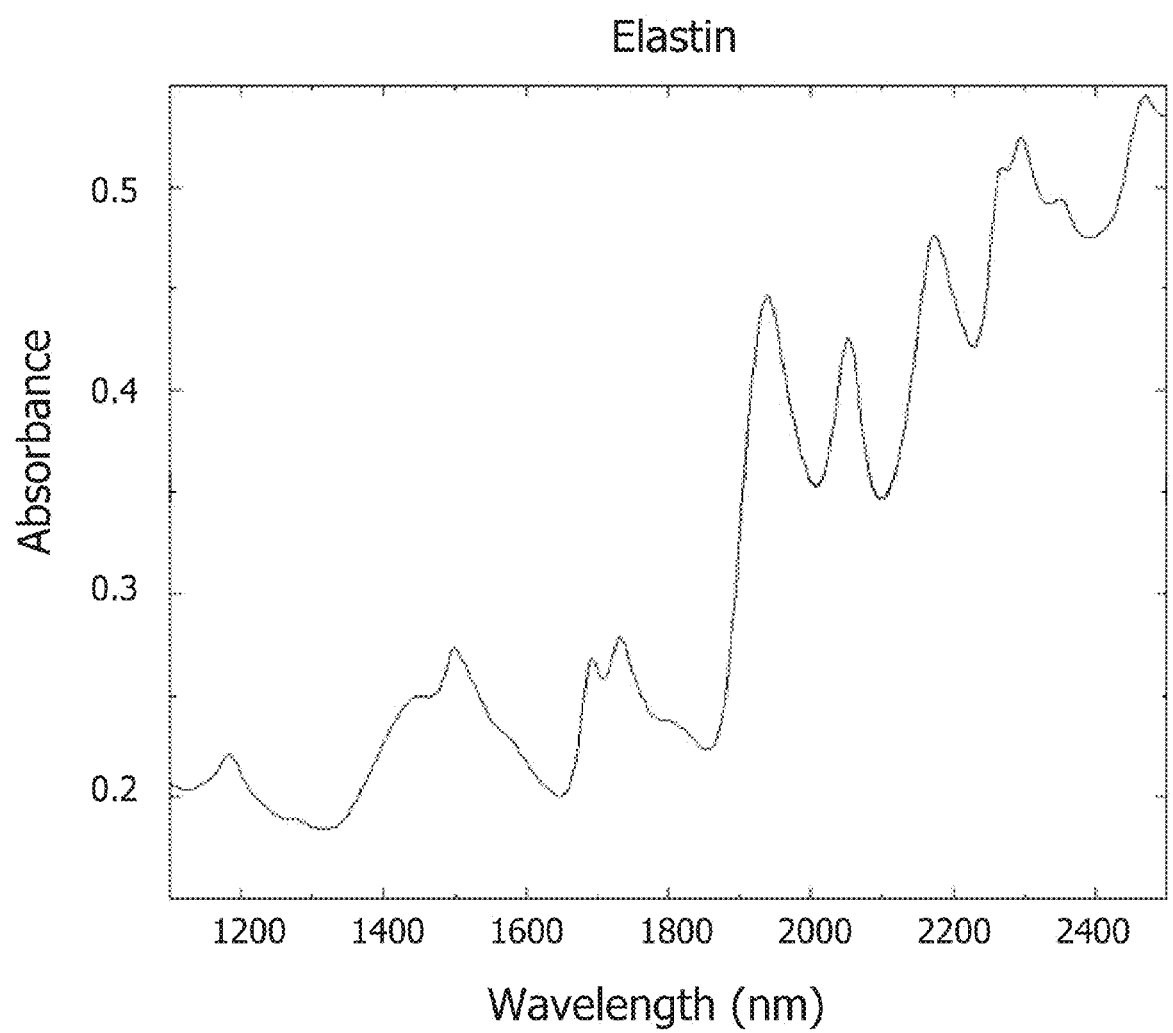

FIGS. 5A-5C illustrate charts for absorption spectrum for gelatin (fragmental collagen) and water (FIG. 5A), Collagen III (FIG. 5B), and Elastin (FIG. 5C). As illustrated in FIGS. 5A-5C water experiences relative less absorption while collagen and elastin have strong absorption in spectral bands between 1400 nm and 2400 nm (excluding the 1900 nm band). Gelatin has similar absorption to collagen and elastin. For skin welding, the energy of pulsed laser 20 having wavelengths in a range of 1500 nm-to 2400 nm can be directly transferred to collagen due to collagen NH and CH overtone and combination mode absorption, i.e., direct collagen excitation. Direct elastin excitation can also occur between 1700 nm-2300 nm. For tissues that absorption of water still dominates in the 2100-2300 nm range, both thermal, non thermal and direct collagen and/or excitation mechanisms play an important role in tissue welding using the pulsed lasers 20. Thermal effect melts the tissue.

Figure 6:
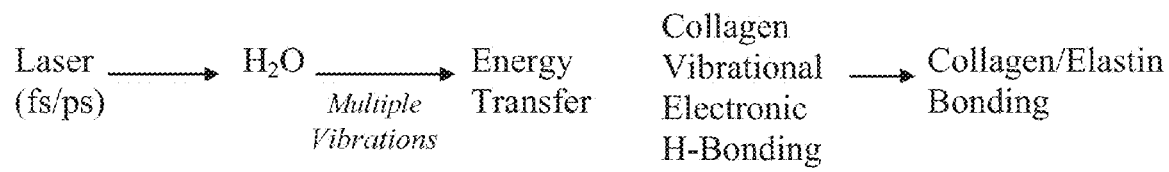
FIG. 6 illustrates direct and indirect welding mechanisms in accordance with the invention.
Figure 6:
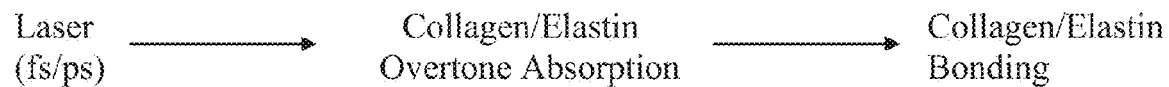

FIG. 6 illustrates direct and indirect welding mechanisms. The type of welding mechanism also is a factor in determining the wavelength. In the indirect non-thermal mechanism, the pulse laser 20 is of a wavelength excites the water in the tissue by vibrational overtones and combination of the primary modes and non-thermally excites the water mediated hydrogen bonds in the collagen (or elastin). The hydrogen bonds are then disrupted and reformed creating the bond. For example, using a ps or fs pulsed laser 20 at a wavelength of 1560+/−30 rim, the excitation of the overtone and combination modes of water molecules in the tissues by targeting the combination mode of water (1, 0, 1) in order to cause energy transfer thus crosslinking the structural proteins especially collagen /elastiri to result in welding of the animal ex vivo and in vivo tissues. Additionally, using wavelengths of about 1064+1−30 rim excites a combination vibrational mode (1, 1, 1).

In the direct excitation of the proteins, the pulsed laser 20 is of a wavelength that excites and causes vibrational overtones and combination modes (absorption) and non-thermally excites the protein by direct energy transfer. The hydrogen bonds are then disrupted and reformed creating the bond.

The pulsed laser 20 can be tunable. A tunable pulsed laser is a laser where the wavelength can be changed. For example, a pulsed laser adapted to be tuned in a wavelength range of 800 nm to 2700 nm can be used. Additionally, fixed pulse laser(s) 20 can be used. Preferably, a single source of light is used. However, multiple pulse lasers can also be used to achieve fusion. If multiple pulsed lasers are used, each pulse can have an average power between 40 miliwatts and 400 miliwatts. Multiple pulses will decrease the weld time.

For example, light sources for the pulsed laser 20 can be based on solid state lasers, semiconductor lasers, fiber lasers, parametric oscillators. Semiconductor lasers including, but not limited to, InGaAs and In GaAsP alloy semiconductor lasers, and AlGaAs quantum well (QW) intraband transition semiconductor lasers can be used. Fiber lasers including, but not limited to, Yb (Ytterbium) doped fiber lasers and Er (Erbium) doped fiber lasers can be used. Solid state lasers including, but not limited to, YAG, glass, Cunyite, forsterite, LIGO, LISO can be used. Also, tunable near-infrared (NIR) lasers based upon the $Cr^{4+}$ active ion, such as, Cr:forsterite lasers with wavelengths tunable from about 1,150 to about 1,350 nm, unyite Cr:CazGe04 lasers tunable from about 1,350 to about 1,500 nm, $Cr^{4+}$YAG lasers tunable from about 1,370 to about 1,600 nm, and LIGOILISO tunable from 1150 to 1600 nm can be used. The unique tuning ranges of these lasers make them attractive as light sources for the tissue welding technique as their simplicity of operation negates the need for the addition complexity of wavelength conversion processes that are required to generate light in the NIR from other lasers. The tunable wavelengths from the lasers offer more versatility in selecting precise depth penetration for laser tissue welding. For example, TOPAS parametric oscillator operates in 1200 to 2700 nm wavelengths. The bonding with 1700 nm wavelength is five times stronger than pumping water.

At S2, other light parameters are adjusted, such as, but not limited to pulse width, power output and power density. The pulse width is on the order of picoseconds or femtoseconds. For example, the pulse width can be less than 10 ps. Average power is between about 40 and 400 miliwatts.

Once, the light source is optimized, the edges of the tissue wound 15 (tissue wound 10) are joined (S3) and the tissue wound 10 is irradiated with the pulsed laser 20 (S4). The tissue wound 10 is irradiated with the pulsed laser 20 until the weld has a desired tensile strength.

During the welding, e.g., active irradiating, the parameters of the light source can be varied as necessary (S5). For example, the pulse width can be cycled to different values. Additionally, both ps and fs pulse widths can be used.

The method disclosed herein can be used with or without a dye or additive or solder.

Comparative Analysis

The method was tested and compared with a Continuous Wave ("CW") LTW and a conventional suture. The conventional suture was used as a control. Guinea pigs were used.

For purposes of the comparative example, the results of an fs IMRA fiber laser at a 1560 nm +/−30 nm with an average power of 100 mW and a CW laser of 1450 nm will be discussed. The pulse rate of the laser is 50 Mhz.

The results of the welding were compared after four periods, immediately after post-op, seven days after, forty-two days and sixty day.

Figure 7A:
Figure 7B:

FIGS. 7A-12B depict the results. FIGS. 7A (H&E) and 7B (Masson's Trichsome) 40× depict a Histology of 1535 nm wavelength fs pulsed laser welded in vivo skin samples of guinea pig GP0013 after 7 postoperative days.

Haematoxylin and eosin (H&E) staining protocol is used frequently in histology to examine thin sections of tissue. Haematoxylin stains cell nuclei blue, while eosin stains cytoplasm, connective tissue and other extracellular substances pink or red. Eosin is strongly absorbed by red blood cells, coloring them bright red. In a skilfully made H & E preparation the red blood cells are almost orange, and collagen and cytoplasm (especially muscle) acquire different shades of pink. Masson's trichrome is a three-colour staining protocol to distinguish cells from surrounding connective tissue. Most recipes will produce red keratin and muscle fibers, blue or green staining of collagen and bone, light red or pink staining of cytoplasm, and black cell nuclei.

The serial sections show well opposed surgical incision with almost complete wound healing in epidermis and granulation tissue in dermis and no significant inflammatory cell infiltration.

Figure 8A:
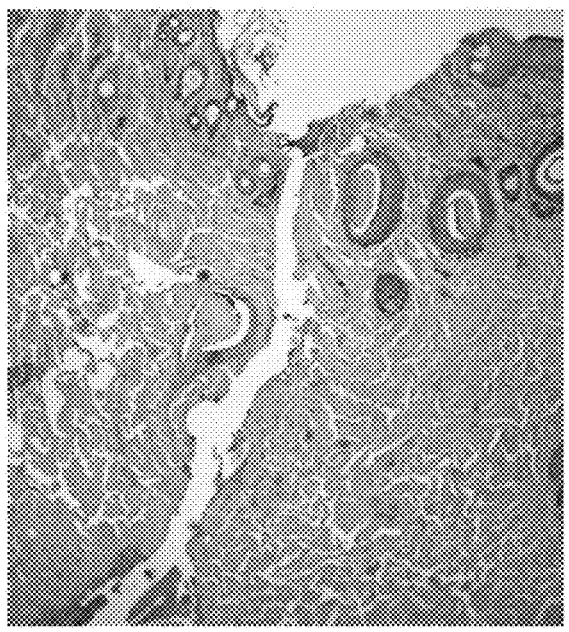
FIGS. 8A and 8B illustrate results from repair with suture after seven postoperative days.
Figure 8B:

FIGS. 8A (H&E) and 8B (Masson's Trichrome) 40× depict a Histology of sutured control surgical incision of guinea pig GPO013 after 7 postoperative days. The serial sections show well opposed surgical incision with very minimal wound healing in epidermis and minimal granulation tissue in dermis and no significant inflammatory cell infiltration.

Figure 9A:
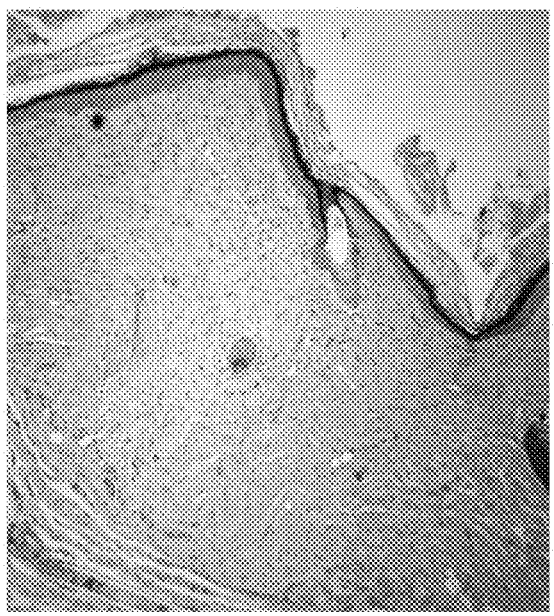
FIGS. 9A and 9B illustrate results of repair with sutures after forty-two postoperative days.
Figure 9B:
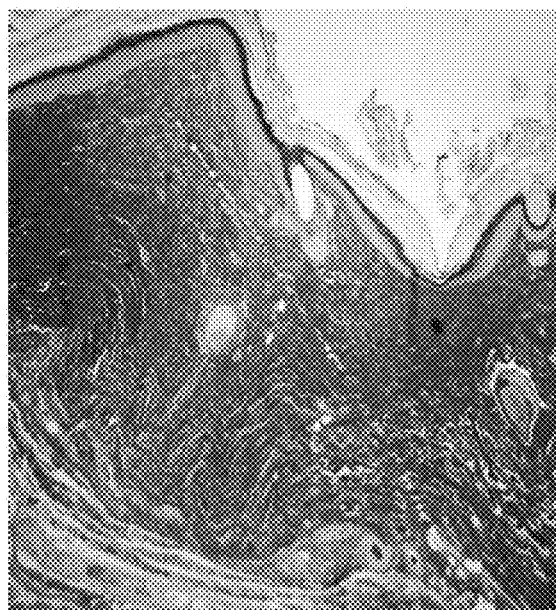

FIGS. 9A (H&E) and 9B (Masson's Trichsome) 40× depicts a Histology of sutured control surgical incision of guinea pig GPO014 after 42 postoperative days. The serial sections show control sutured surgical incision wound healing in epidermis with hyperkeratinized stratified squamous epithelium and extensive and irregular dermal collagen fiber deposition in dermis, lack of hair follicles and there is no significant inflammatory cell infiltration.

Figures 10A, 10B:
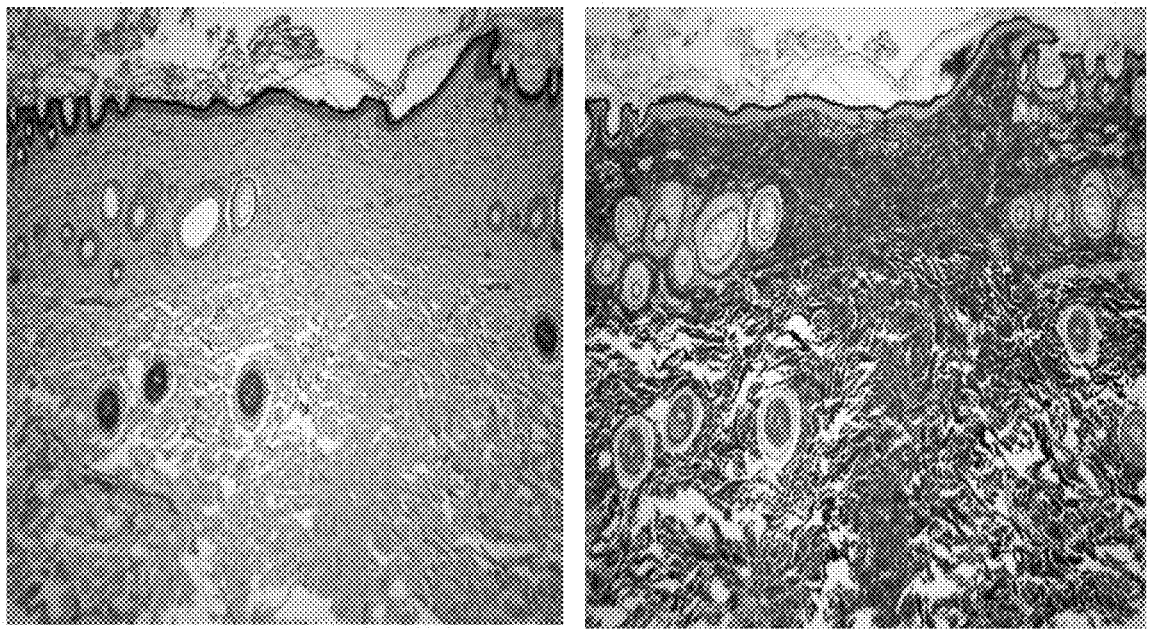
FIGS. 10A and 10B illustrate CW laser repair after forty-two postoperative days.

FIGS. 10A (H&E) and 10B (Masson's Trichrome) 40× depict a Histology CW laser welded surgical incision of guinea pig GPO014 after 42 postoperative days. The serial sections show CW NIR laser at 1450 nm welded surgical incision wound healing in epidermis with almost normal stratified squamous epithelium and minimal irregular collagen fiber deposition in dermis. The lack of hair follicles confined only to weld line and no significant inflammatory cell infiltration.

Figures 11A, 11B:
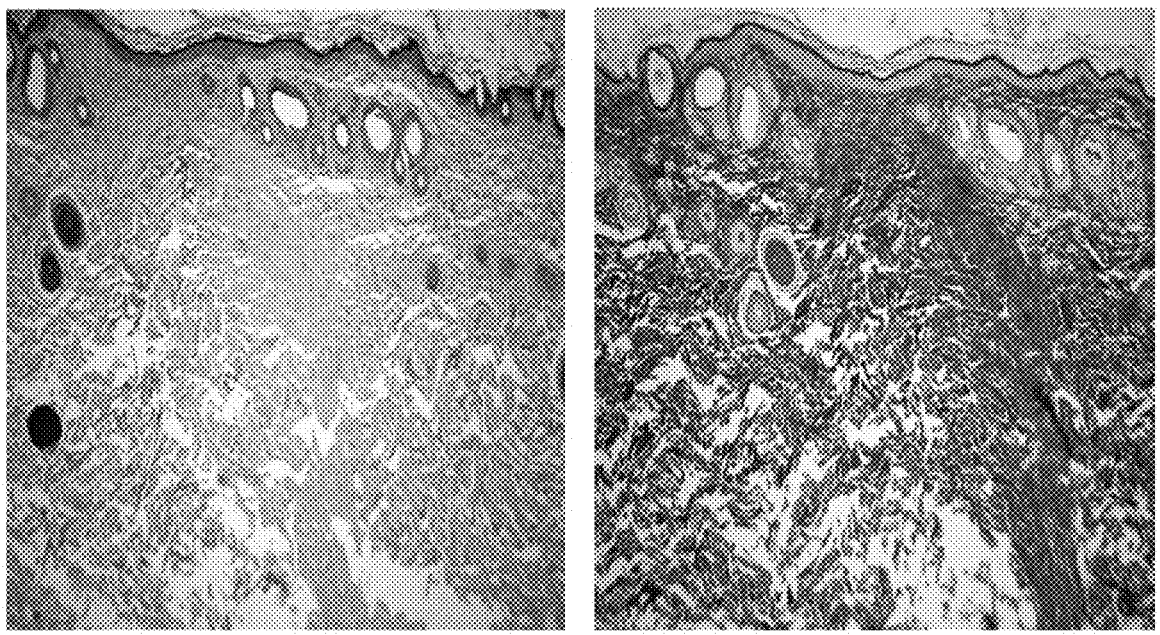
FIGS. 11A and 11B illustrate Femtosecond pulsed laser repair after forty-two postoperative days and FIG. 12A illustrates in vivo guinea pig immediately after welding and FIG. 12B at sixty days post-op.

FIGS. 11A (H&E) and 11B (Masson's Trichsome) 40× depicts a Histology of FS IMRA surgical incision of guinea pig GPO014 after 42 post operative days. The serial sections show fs pulsed laser welded surgical incision wound healing in epidermis with almost normal stratified squalnous epithelium and very minimal irregular collagen fiber deposition in dermis. The lack of hair follicles confined only to weld line and no significant inflammatory cell infiltration.

Figure 12A:
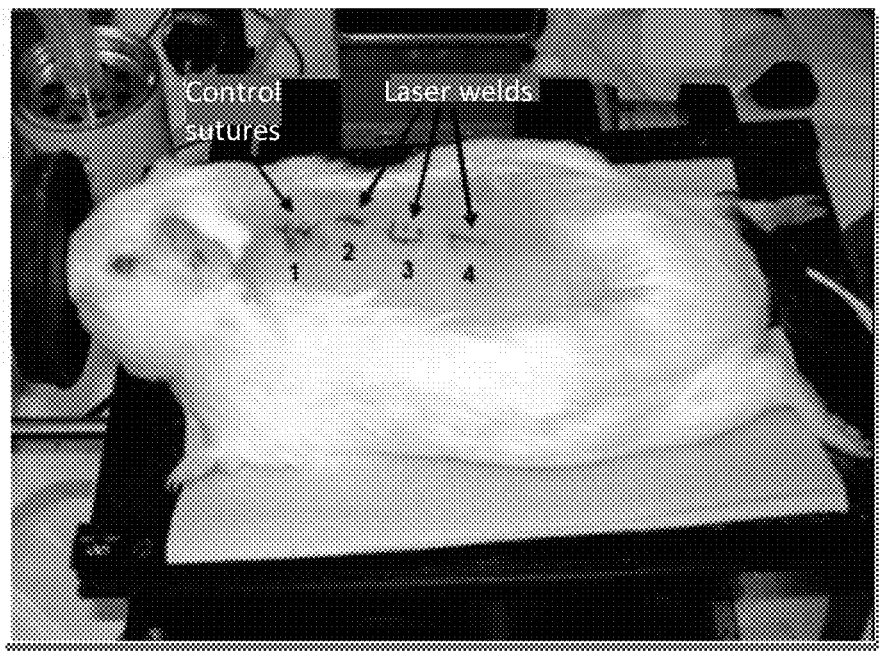
Figure 12B:
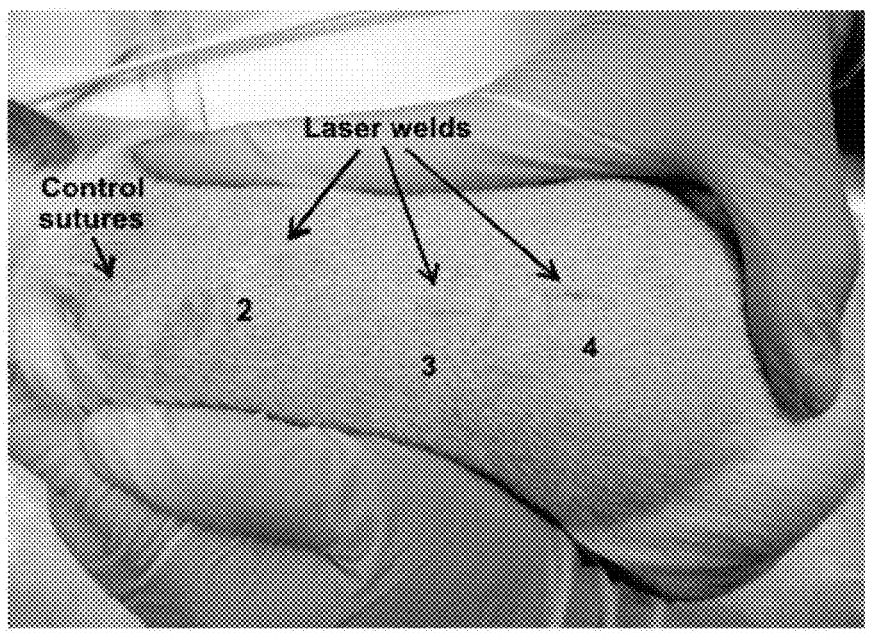

FIG. 12A depicts an in vivo guinea pig immediately after welding and FIG. 12B at sixty days post-op. Incision 2 was welded with fs pulsed laser, incisions 3 and 4 were welded with CW laser and incision 1 was sutured.

The histopathology of H&E and Masson's trichrome stained serial sections of in vivo laser welded skin tissues suggests that the use of CW and fs pulsed laser at 90-100 mW power yielded better weld quality and post operative healing than the suture control. LTW resulted in very minimal scar formation in the tissue when compared to the suture controls. The Guinea pig GPO013 was sacrificed on post operative day 7 to evaluate the wound healing pattern and tissue regeneration.

The control sutured skin from same animal (FIGS. 8A & 8B) show poor healing, very minimal granulation tissue and more loss of dermal appendages. The late effects laser tissue welding evaluated in guinea pig GPO014 revealed minimal scar tissue formation and minimal loss of dermal appendages with laser welds than the control sutured tissues. The fs pulse laser welds (FIGS. 11A & 11B) have minimal residual effects of wound healing and much better healing pattern than CW welded tissues (FIGS. 10A & 10B). The guinea pigs are shown in FIGS. 12A and 12B exhibit minimal thermal effects using fs pulsed laser. The IMRA fs 1560 nm laser for many in vivo animal studies with an average power of 100 mW with increase in total weld times resulted in the minimal thermal damage compared CW 1450 nm laser welding.

By using the ultrashort ps or fs pulsed laser(s) 20, collateral thermal damage is reduced enabling welding tissue at larger spot size which is confirmed by the study. The welding by using ps or fs pulsed laser(s) 20 allows the water in the collagen helix to absorb the pulse energy without collateral damage. The water is immediately raised to a much higher temperature than the surrounding tissue. This excitation breaks the $H_2O$ mediated inter and intra chain collagen bonds and results in partial denaturing of the collagen. After the water cools, the bonds reform and reestablish hydrogen bonding in some of the renatured helix. Because the time between laser pulses is long compared to the pulse width, the average power can be lower than for CW welding. However, the instantaneous power can be high, e.g., sufficiently high pulse energy to can tissue ablation.

Additionally, since the vibrational relaxation time of the water is less than the time between laser pulses, the water molecules have time to relax to background tissue temperature. This can reduce the average tissue temperature and possibly reduce the extent of dehydration.

The pulsed laser 20 having a pulse width less than the vibrational relaxation time, e.g., 1-5 ps, achieved a good welding strength.

LTW using fs pulsed laser through a direct protein excitation mechanism, e.g., wavelengths in the range of 1400 nm to 2400 nm, can provide a bonding while also using a low power since the collagen/elastin overtones and combination modes are mostly excited directly and have no need for energy transfer by heat generation from water absorption. Better bonding at lower powers and a faster scan rate from directly exciting of collagen/elastin is achieved than just indirect energy transfer using heat generated from water absorption. The tissue welding at 1400-2400 nm was obtained using the tunable fs lasers output from a Topaz parametric oscillator pumped by a high-power femtosecond Ti:sapphire laser consisting of an oscillator (Spectra Physics Tsunami), a regenerative amplifier (Quantronix Model 4810) and a custom-built multi-pass amplifier currently in operation at the PI's laboratory—Institute for Ultrafast Spectroscopy and Lasers at CCNY.

However, some energy transfer between water and collagen/elastin molecules using the 1400-2400 nm ranges will also occur.

The methods described above are illustrative examples and it should not be construed that the present invention is limited to these particular embodiments. Thus, various changes and modifications may be effected by one skilled in the art without departing from the spirit or scope of the invention as defined in the appended claims.

What is claimed is:

1. A method for welding tissue wounds in an animal/human, comprising:
    joining edges of a tissue wound; and
    irradiating the tissue wound and tissue surrounding the tissue wound with a pulsed laser, the pulsed laser having a laser wavelength in a range of an absorption band of native tissue molecules of water, elastin and/or collagen in the tissue wound and the tissue surrounding the tissue wound, said pulsed laser having a pulse width of not more than picoseconds in order of magnitude, said pulsed laser non-thermally inducing vibration modes of tissue surrounding the tissue wound and facilitates bonding of native tissue protein present in the tissue surrounding the tissue wound to achieve tissue repair.

2. The method of claim 1, wherein the laser wavelength is in a range of between about 800 nm to about 2,700 nm to photon excite vibrational modes of water, collagen or elastin from absorption.

3. The method of claim 1, wherein said pulsed laser is a picosecond laser.

4. The method of claim 1, wherein said pulsed laser is a femtosecond laser.

5. The method of claim 1, where said pulsed laser has a pulse width of less than 10 picoseconds.

6. The method of claim 1, wherein the tissue wound is to tissue selected from a group consisting of skin, mucosal tissue, bone, blood vessels, artery, neural tissue, hepatic tissue, pancreatic tissue, splenic tissue, renal tissue, bronchial tissue, tissues of the respiratory tract, tissues of the urinary tract, tissues of the gastrointestinal tract and tissues of the gynecologic tract.

7. The method of claim 6, wherein the tissue wound is a fistula of the gastrointestinal tract.

8. The method of claim 6, wherein the tissue wound is a fistula of the urinary tract.

9. The method of claim 6, wherein the tissue wound is air leak in pulmonary tissue.

10. A method for welding tissue wounds in an animal/human comprising:
    joining edges of a tissue wound; and
        irradiating the tissue wound and tissue surrounding the tissue wound with a picosecond or a femtosecond pulsed laser, said picosecond or said femtosecond pulsed laser irradiated energy being selected to be within a range of absorption of native tissue molecules for non-thermally inducing molecular crosslinking of native tissue proteins surrounding the tissue wound and facilitates bonding of native tissue proteins present in the tissue surrounding the tissue wound to achieve tissue fusion.

11. The method of claim 10, wherein said picosecond or said femtosecond pulsed laser is selected from a group consisting of picosecond or femtosecond solid state lasers, semiconductor lasers and fiber lasers, YAG glass lasers, and parametric oscillator lasers.

12. The method of claim 10, wherein said picosecond or said femtosecond pulsed laser is tuned to a spectral range which corresponds to an absorption band of water in the tissue wounds and tissue proteins surrounding the wounds at wavelengths about 1064+1–30 nm, 1450+/–30rn n, 1560+/–30nm, 1950+/–30nm and 2400+/–30nm.

13. The method of claim 12, wherein in said irradiating, said water in the tissue wound and the tissue proteins surrounding the tissue wound absorbs energy from said picosecond or femtosecond pulsed laser by vibrational overtones and combinations of primary modes (v1, v2, v3) and non-thermally excites water mediated hydrogen bonds in collagen and elastin molecules due to energy transfer and wherein said picosecond or said femtosecond pulsed laser have wavelengths of about 1560+/–30 nm and energy at these wavelength excites a combination mode (1, 0, 1) of water and wavelengths of about 1064+/–30 nm excites a combination mode(1, 1, 1).

14. The method of claim 10, wherein said picosecond or said femtosecond pulsed laser is tuned to a spectral range which corresponds to an absorption band of collagen in the tissue wounds and tissue proteins surrounding the tissue wounds at wavelengths about 1750+/–30nm, 2050+/–30nm, 2200+/–30nm, and 2300+/–30nm.

15. The method of claim 14, wherein in said irradiating, said tissue proteins absorb energy from said picosecond or said femtosecond pulsed laser by vibrational overtones and combinations modes(v1, v2, v3) and non-thermally excites collagen molecules by direct energy transfer and wherein energy of said picoseconds or said femtosecond pulsed laser at these wavelengths excites combination modes, and overtone vibrational modes of the collagen.

16. The method of claim 10, where said picosecond or said femtosecond pulsed laser is tuned a spectral range which corresponds to an absorption band of elastin in the tissue wound and tissue proteins surrounding the tissue wound at wavelengths about 1700+/–30nm, 2050+/–30nm, 2200+/–30nm, and 2300+/–30nm.

17. The method of claim 16, wherein in said irradiating, said tissue proteins absorb energy from said picosecond or said femtosecond pulsed laser by vibrational overtones and combinations rnodes(v1, v2, v3) and non-thermally excites elastin molecules by direct energy transfer and wherein energy of said picosecond or said femtosecond pulsed laser at these wavelengths excites combination modes, and overtone vibrational modes of the elastin.

18. The method of claim 10, wherein average power of said picosecond or said femtosecond pulsed laser is in a range of about 40 milliwatts to about 5400 milliwatts to induce non-thermal mechanisms of reversible dissociation of intramolecular, inteituolecular hydrogen bonds, electrostatic interactions in tissue proteins surrounding said tissue wound.

19. The method of claim 10, wherein average power of said picosecond and said femtosecond pulsed lasers is in a range of about 100 milliwatts to about 1600 milliwatts to induce non-thermal vibrations of intramolecular, intermolecular hydrogen bonds, electrostatic interactions in tissue proteins surrounding said tissue wound.

20. The method of claim 10, wherein said tissue wound is to tissue selected from a group consisting of skin, mucosal tissue, bone, blood vessels, artery, neural tissue, hepatic tissue, pancreatic tissue, splenic tissue, renal tissue, bronchial tissue, tissues of the respiratory tract, tissues of the urinary tract, tissues of the gastrointestinal tract and tissues of the gynecologic tract, tissues of male reproductive system.

21. The method of claim 10, wherein said picosecond or femtosecond pulsed laser has a pulse width of less than 10 ps for tissue welding using a wavelength in a range of about 900 nm to about 2700 nm.

22. The method of claim 10, wherein both picosecond and femtosecond pulses are emitted from said picosecond or femtosecond pulsed laser.

23. The method of claim 10, wherein a plurality of picosecond or femtosecond pulsed lasers irradiate the tissue wound and tissue surrounding the tissue wound.

24. A method for welding tissue wounds in animals comprising the steps of:
joining edges of a tissue wound; and irradiating the tissue wound and tissue surrounding the tissue wound with a picosecond or a femtosecond pulsed laser, said picosecond or said femtosecond pulsed laser irradiated energy being selected to be within a range of absorption of native tissue molecules inducing molecular crosslinking of native tissue proteins surrounding the tissue wound and facilitates bonding of native tissue proteins present in the tissue surrounding the tissue wound to achieve tissue fusion, said picosecond or said femtosecond pulsed laser being tuned to a spectral range which corresponds to an absorption band of collagen in the tissue wound and tissue proteins surrounding the tissue wounds causing said tissue proteins to absorb energy from said picosecond or said femtosecond pulsed laser by vibrational overtones and combination modes and non-thermally excites collagen molecules by direct energy transfer and wherein energy of said picoseconds or said femtosecond pulsed laser at these wavelengths excites combination modes, and overtone vibrational modes of the collagen.

* * * * *